(12) United States Patent
Sugio et al.

(10) Patent No.: US 7,601,530 B2
(45) Date of Patent: Oct. 13, 2009

(54) BACTERIA STRAIN WENELEN DSM 16786, USE OF SAID BACTERIA FOR LEACHING OF ORES OR CONCENTRATES CONTAINING METALLIC SULFIDE MINERAL SPECIES AND LEACHING PROCESSES BASED ON THE USE OF SAID BACTERIA OR MIXTURES THAT CONTAIN SAID BACTERIA

(75) Inventors: Tsuyoshi Sugio, Okayama (JP); Akira Miura, Colina (CL); Pilar A. Parada Valdecantos, Colina (CL); Ricardo Badilla Ohlbaum, Colina (CL)

(73) Assignee: Biosigma S.A., Colina (CL)

( * ) Notice: Subject to any disclaimer, the term of this patent is extended or adjusted under 35 U.S.C. 154(b) by 346 days.

(21) Appl. No.: 11/256,221

(22) Filed: Oct. 21, 2005

(65) Prior Publication Data

US 2006/0094094 A1 May 4, 2006

(30) Foreign Application Priority Data

Oct. 22, 2004 (CL) ................................. 2731-2004

(51) Int. Cl.
*C12N 1/20* (2006.01)
(52) U.S. Cl. .................................... 435/252.1; 424/93.1
(58) Field of Classification Search ........................ None
See application file for complete search history.

(56) References Cited

U.S. PATENT DOCUMENTS

| | | | |
|---|---|---|---|
| 4,571,387 | A | 2/1986 | Bruynesteyn et al. |
| 4,732,608 | A | 3/1988 | Emmett, Jr. et al. |
| 5,429,659 | A | 7/1995 | Spencer et al. |
| 5,919,674 | A | 7/1999 | Tunley |
| 6,096,113 | A | 8/2000 | Schaffner |
| 6,110,253 | A | 8/2000 | Kohr et al. |
| 6,146,444 | A | 11/2000 | Kohr |
| 6,168,766 | B1 | 1/2001 | Imai et al. |
| 6,245,125 | B1 | 6/2001 | Dew et al. |
| 6,387,155 | B1 | 5/2002 | Kohr |
| 6,387,239 | B1 | 5/2002 | Duyvesteyn et al. |
| 2003/0167879 | A1 | 9/2003 | Batty et al. |

FOREIGN PATENT DOCUMENTS

| | | |
|---|---|---|
| CA | 2 374 509 A1 | 11/2000 |
| CA | 2 282 848 A1 | 3/2001 |
| CA | 2 381 157 A1 | 3/2001 |
| CN | 1204691 | 1/1999 |
| EP | 0 004 431 B1 | 9/1981 |
| GB | 1 528 061 | 10/1978 |
| WO | 00/23629 | 4/2000 |
| WO | 01/44519 A1 | 6/2001 |

OTHER PUBLICATIONS

Nowaczyk et al., Polish Journal of Environmental Studies vol. 9, No. 3 (2000), 195-201.*
Abdel-Fattah et al. "Numerical Modeling of Ferrous-ion Oxidation Rate in *Acidithiobacillus ferrooxidans* ATCC 23270: Optimization of Culture Conditions Through Statistically Designed Experiments." *Acta Microbiologica Polonica*. vol. 51. No. 3. 2002. pp. 225-235.
Coram et al. "Molecular Relationship between Two Groups of the Genus *Leptospirillum* and the Finding that *Leptospirillum ferriphilum* sp. nov. Dominates South African Commercial Biooxidation Tanks That Operate at 40°C." *Applied & Environ. Microbiology*. vol. 68. No. 2. 2002. pp. 838-845.
Espejo et al. "Bacterial Community in Copper Sulfide Ores Inoculated and Leached with Solution from a Commercial-Scale Copper Leaching Plant." *Applied & Environ. Microbiology*. vol. 63. No. 4. 1997. pp. 1344-1348.
Kelly et al. "Reclassification of some species of *Thiobacillus* to the newly designated genera *Acidithiobacillus* gen. nov., *Halothiobacillus* gen. nov. and *Thermithiobacillus* gen. nov." *Int Jr. of Systematic and Evolutionary Microbiology*. vol. 50. 2000. pp. 511-516.
Levenspiel . "Chemical Reaction Engineering: An Introduction to the Design of Chemical Reactors." *Wiley International Edition*. First Edition 1966. pp. 344-350.
Lowry et al. "Protein Measurement with the Folin Phenol Reagent." *Jr. of Biological Chemistry*. vol. 1. 1951. pp. 265-275.
Okibe et al. "Enumeration and Characterization of Acidophilic Microorganisms Isolated from a Pilot Plant Stirred-Tank Bioleaching Operation." *Applied & Environ. Microbiology*. vol. 69. No. 4. 2003. pp. 1936-1943.

(Continued)

*Primary Examiner*—Irene Marx
(74) *Attorney, Agent, or Firm*—Merchant & Gould P.C.

(57) ABSTRACT

The present invention is related to an isolated chemolithotrophic bacterial strain belonging to the specie *Acidithiobacillus ferrooxidans*, named "Wenelen" and deposited at the Deutsche Sammlung von Mikroorganismen und Zellkulturen GmbH—DSMZ under classification number DSM 16786, the use of said bacteria for leaching ores or concentrates containing of metallic sulfide species and leaching processes based on the use of said bacteria or mixtures that contain said bacteria. This Wenelen DSM 16786 strain has an increased oxidizing activity, especially regarding chalcopyrite, when compared to known bacteria. Due to the former feature, this bacteria strain show great interest for biomining applications and it is presently being subjected to annotation processes after sequencing.

6 Claims, 4 Drawing Sheets

OTHER PUBLICATIONS

Peters. "Direct Leaching of Sulfides: Chemistry and Applications." *Metallurgical Transactions.* vol. 7B. 1976. pp. 505-517.

Pizarro et al. "Bacterial Populations in Samples of Bioleached Copper Ore as Revealed by Analysis of DNA Obtained before and after Cultivation." *Applied & Environ. Microbiology.* vol. 62. No. 4. 1996. pp. 1323-1328.

Rawlings et al. "Biomineralization of metal-containing ores and concentrates." *TRENDS in Biotechnology.* vol. 21. No. 1. 2003. pp. 38-44.

Rawlings. "Heavy Metal Mining Using Microbes." *Annu. Rev. Microbiol.* vol. 56. 2002. pp. 65-91.

Sugio et al. "Existence of a Hydrogen Sulfide: Ferric Ion Oxidoreductase in Iron-Oxidizing Bacteria." *Applied & Environ. Microbiology.* vol. 58. No. 1. 1992. pp. 431-433.

Tshilimbo et al. "Mechanism and kinetics of chalcopyrite passivation during bacterial leaching." *COOPER 2003-COBRE 2003. Volume VI-Hydrometallurgy of Copper (Book 1).* 2003. pp. 99-116.

Uhrie et al. "The metallurgical development of the Morenci MFL project." *COOPER 2003-COBRE 2003. Volume VI-Hydrometallurgy of Copper (Book 1).* 2003. pp. 29.37.

* cited by examiner

TGGAGAGTTTGATCCTGGCTCAGATTGAACGCTGGCGGCATGCCTAACACATG
CAAGTCGAACGGTAACAGGTCTTCGGATGCTGACGAGTGGCGGACGGGTGAGT
AATGCGTAGGAATCTGTCTTTTAGTGGGGGACAACCCAGGGAAACTTGGGCTA
ATACCGCATGAGCCCTGAGGGGGAAAGCGGGGGATCTTCGGACCTCGCGCTAA
GAGAGGAGCCTACGTCCGATTAGCTAGTTGGCGGGGTAAAGGCCCACCAAGG
CGACGATCGGTAGCTGGTCTGAGAGGACGACCAGCCACACTGGGACTGAGAC
ACGGCCCAGACTCCTACGGGAGGCAGCAGTGGGGAATTTTTCGCAATGGGGGC
AACCCTGACGAAGCAATGCCGCGTGGATGAAGAAGGCCTTCGGGTTGTAAAGT
CCTTTCGTGGAGGACGAAAAGGTGGGTTCTAATACAATCTGCTATTGACGTGA
ATCCAAGAAGAAGCACCGGCTAACTCCGTGCCAGCAGCCGCGGTAATACGGG
GGGTGCAAGCGTTAATCGGAATCACTGGGCGTAAAGGGTGCGTAGGCGGTAC
GTTAGGTCTGTCGTGAAATCCCCGGGCTCAACCTGGGAATGGCGGTGGAAACC
GGTGTACTAGAGTATGGGAGAGGGTGGTGGAATTCCAGGTGTAGCGGTGAAAT
GCGTAGAGATCTGGAGGAACATCAGTGGCGAAGGCGGCCACCTGGCCCAATA
CTGACGCTGAGGCACGAAAGCGTGGGGAGCAAACAGGATTAGATACCCTGGT
AGTCCACGCCCTAAACGATGAATACTAGATGTTTGGTGCCTAGCGTACTGAGT
GTCGTAGCTAACGCGATAAGTATTCCGCCTGGGAAGTACGGCCGCAAGGTTAA
AACTCAAAGGAATTGACGGGGGCCCGCACAAGCGGTGGAGCATGTGGTTTAAT
TCGATGCAACGCGAAGAACCTTACCTGGGCTTGACATGTCCGGAATTCTGCAG
AGATGCGGAAGTGCCCTTCGGGGAATCGGAACACAGGTGCTGCATGGCTGTCG
TCAGCTCGTGTCGTGAGATGTTGGGTTAAGTCCCGCAACGAGCGCAACCCTTG
TCCTTAGTTGCCAGCGGTTCGGCCGGGCACTCTAGGGAGACTGCCGGTGACAA
ACCGGAGGAAGGTGGGGATGACGTCAAGTCCTCATGGCCTTTATGTCCAGGGC
TACACACGTGCTACAATGGCGCGTACAGAGGGAAGCCAAGCCGCGAGGTGGA
GCAGACCCCAGAAAGCGCGTCGTAGTTCGGATTGCAGTCTGCAACTCGACTGC
ATGAAGTCGGAATCGCTAGTAATCGCGGATCAGCATGCCGCGGTGAATACGTT
CCCGGGCCTTGTACACACCGCCCGTCACACCATGGGAGTGGATTGTACCAGAA
GCAGCTAGCCTAACCTTCGGGAGGGCGGTTACCACGGTATGGTTCATGACTGG
GGTGAAGTCGTAACAAGGTAGCCGTAGGGGAACCTGCGGCTGGATCACCTCCT
T

BACTERIA STRAIN WENELEN DSM 16786, USE OF SAID BACTERIA FOR LEACHING OF ORES OR CONCENTRATES CONTAINING METALLIC SULFIDE MINERAL SPECIES AND LEACHING PROCESSES BASED ON THE USE OF SAID BACTERIA OR MIXTURES THAT CONTAIN SAID BACTERIA

The present invention is related to an isolated chemolithotrophic bacterial strain belonging to the species *Acidithiobacillus ferrooxidans*, named "Wenelen" and deposited under the Budapest Treaty with the Deutsche Sammiung von Mikroorganismen und Zellkulturen GmbH —DSMZ, having an address of Mascheroder Weg 1b, D-38124 Braunschweig, Germany, under classification number DSM 16786, on Oct. 7, 2004, the use of said bacteria for leaching of ores or concentrates of sulfide minerals and leaching processes based on the use of said bacteria or mixtures that contain said bacteria. This Wenelen DSM 16786 strain has an increased oxidizing activity, especially regarding chalcopyrite, when compared to known bacteria. Due to the former feature, this strain show great interest for biomining applications and it is presently being subjected to annotation processes after sequencing.

BACKGROUND OF THE INVENTION

Presently, more than 90% of the mineable copper in the world is obtained by processing copper sulfide minerals. Among the copper sulfide present in minerals, chalcopyrite, bornite, chalcosite, covellite, tennantite and enargite, chalcopyrite are the most relatively abundant species and being therefore the most economically interesting species.

Nowadays, the processing of copper sulfide minerals is built upon technologies based in physical and chemical processes associated to mineral crushing, grinding and flotation, followed by melting-conversion of concentrate and electrolytic refining of metals. In the general practice, more than 80% of copper is produced by the processes that follows the described route—called conventional route—, which is limited to high and medium grade minerals, depending on the specific characteristics of the mineral ores and the mineral processing plants. Due to this fact, there are vast and valuable mineral resources having relatively low mineral grades that are sub-economical when conventional technologies are used and remain unexplored due to the lack of an effective technology for their exploitation.

On the other hand, minerals in which copper is present as oxidized species—readily soluble in acid—are processed using acid leaching processes, followed by solvent extraction processes and metal electrowinning, in which constitutes the hydrometallurgical route for copper obtaining. This route is very attractive due to its lower operational and investment costs when compared to conventional technologies and due to its lower environmental impact. However, the application of this technology is limited to oxidized minerals or to the case of mixed copper sulfide minerals in which the metal is present as secondary sulfides (chalcosite or covellite), which are acid-soluble when a strong microorganism-catalyzed oxidizing agent is present (Uhrie, J L, Wilton, L E, Rood, E A, Parker, D B, Griffin, J B and Lamana, J R, 2003, "The metallurgical development of the Morenci MFL Project", Copper 2003 Int Conference Proceedings, Santiago, Chile, Vol. VI, 29-39).

In the case of low grade minerals, the only effective technology is their processing in heaps or dumps of ores in which the metal is present as acid-soluble species (oxides) or species that are soluble when bacteria are present (minerals having secondary sulfides such as chalcosite and covellite), which are very rare minerals. Due to this reason, it is essential for sustainable mining expansion to develop a technological break that allows economical processing of minerals having high contents of primary sulfides as chalcopyrite, which are nowadays unexploitable by traditional technologies.

It has been well established that leaching or solubilization of sulfured minerals is favored by the presence of bacteria that oxidize iron and sulfur (see, for instance, the recent review of Rawlings Del.: "Biomineralization of metal-containing ores and concentrates", TRENDS in Biotechnology, Vol. 21 No. 1, p 38-42, 2003). In the exploitation of these minerals by means of heap or dump leaching at commercial scale using mesophilic microorganisms in the range of 25-45° C., satisfactory recoveries and extraction rates of 85% recovery in 270 days of operation are obtained—for leaching of secondary sulfides as covellite (CuS) and chalcosite ($CU_2S$). In this temperature range, the more widely described bacteria at the moment belongs to genera *Acidithiobacillus* and *Leptospirillum*, among which the most common species are *A. ferrooxidans*, *A. thiooxidans*, and *L. ferrooxidans* (Espejo, R T and Romero, J., 1997, "Bacterial community in copper sulfide ores inoculated and leached with solutions from a commercial-scales copper leaching plant", Applied & Environmental Microbiology, Vol. 63, 4, 183-187).

However, for the case of chalcopyrite ($CuFeS_2$) minerals, known microorganisms show a very low leaching rate, therefore copper fractions recovered from chalcopyrite are considered insignificant in industrial labor. A possible explanation, among many others, is the formation of a film over the surface of chalcopyrite that could stop the copper dissolution process (Tshilombo and Dixon DG, "Mechanism and kinetics of chalcopyrite passivation during bacterial leaching". Proceedings of Copper 2003, 5th international conference Vol. VI book 1, p 99-116).

High temperatures in the range of 75-80° C. are used to avoid the passivation process and to obtain recoveries that make the process economical (Rawlings Del., "Heavy metal mining using microbes". Annu Rev Microbiol.; 56:65-91. 2002). For instance, the BioCOP™ process being operated in Chuquicamata, Chile, by Codelco and BHP-Billiton, uses extreme thermophilic microorganisms (archaea) in stirred tanks, as revealed in U.S. Pat. No. 6,110,253 and US 20030167879. The conditions attained in leaching tanks for concentrate leaching are not commercially feasible using mineral processing in vats, heaps, dumps, tailing dams and in situ leaching operations.

In chalcopyrite mineral leaching at industrial scale, many microorganisms have been found; for instance, the use of microorganisms belonging to genera *Leptospirillum* and *Sulfobacillus* has been described (Okibe N, Gericke M, Hallberg K B, Johnson D B., "Enumeration and characterization of acidophilic microorganisms isolated from a pilot plant stirred-tank bioleaching operation." Appl Environ Microbiol. 2003, 69(4):1936-43), however the difficulties found in their isolation, growth and storage make their use complex. Other relevant organisms in bioleaching processes are *Acidithiobacillus*, which present a large diversity with genome homologies ranging between 60-70% intra species and as low as 20-30% inside the genus. Patent EP0004431 refers to the use of the species *Thiobacillus ferrooxidans* (now designated as *Acidithiobacillus ferrooxidans*) for chalcopyrite leaching, with strains that can operate at pH 1.0, but requiring forced aeration. Other examples of this species are strains deposited in the American Type Culture Collection, ATCC 19,859, ATCC 33,020 (Sugio T, et al. "Existence of a hydrogen sulfide:ferric ion oxidoreductase in iron-oxidizing bacteria."

Appl. Environ. Microbiol. 58: 431-433, 1992.), ATCC 23,270, (Abdel-Fattah et al. "Numerical modeling of ferrous-ion oxidation rate in *Acidithiobacillus ferrooxidans* ATCC 23270: optimization of culture conditions through statistically designed experiments" Acta Microbiol Pol. 2002; 51(3): 225-35), etc. However, none of them shows a satisfactory activity with regard to the recovery percentage of copper or the recovery rate thereof.

DESCRIPTION OF THE INVENTION

For a better understanding of the processes herein described, the following definitions apply:
  a) Bioleaching of minerals in vats: process that is carried out in a reservoir (vat) having a false floor wherein the mineral is charged and flooded with a leaching solution, which is circulated through the mineral particles, in the presence of acidophilic microorganisms, the dissolved copper being extracted in an acid solution.
  b) Bioleaching of minerals in stirred tanks or reactors: the bioleaching process is carried out in a mechanically stirred tank where finely divided minerals are mixed with a leaching solution, thus forming a slurry with a solid content up to 20%, in the presence of acidophilic microorganisms, the dissolved copper being extracted in an acid solution.
  c) Bioleaching of minerals in heaps: in this process, mineral ground down to a definite granulometry is accumulated over an impermeable surface having a small slope and the leaching solution is distributed over the surface, in the presence of acidophilic microorganisms, the dissolved copper being extracted at the bottom in an acid solution.
  d) Bioleaching of minerals in dumps: minerals below the grade cut-off that are extracted from an open-pit mine are accumulated "run-of-mine" or after a primary crushing, in a ground crack or fissure with suitable characteristics for the control of solution infiltrations or over surfaces previously treated with an impermeable covering, and the leaching solution is distributed over the surface, in the presence of acidophilic microorganisms, the dissolved copper being extracted at the bottom in an acid solution.
  e) Bioleaching of tailing dams: the bottoms obtained from a flotation process having lesser amounts of the metal that is present in the mineral are accumulated in dams, being extracted therefrom for leaching either in heaps or in stirred tanks, in the presence of acidophilic microorganisms, the dissolved copper being extracted in an acid solution.
  f) In situ mineral bioleaching: mineral ores either natural or fractured in previous mining operations are leached directly in place distributing the leaching solution over the surface, in the presence of acidophilic microorganisms, the dissolved copper being extracted at the bottom in an acid solution.
  g) Inoculum: pure or mixed bacterial culture that will act as active biological material during the bioleaching process.
  h) ATCC: American Type Culture Collection.
  i) DSMZ: Deutsche Sammlung von Mikroorganismen und Zellkulturen GmbH, German Type Culture Collection.
  j) PCR: polymerase chain reaction that allows amplification or "copying" of a DNA fragment.

An isolation strategy for microorganism strains presenting a high specific activity for copper extraction was developed in order to increase copper extraction from samples obtained from mining processes. Samples were enriched in stirred flasks with modified 9K medium (3.0 g/L $(NH_4)_2SO_4$, 0.5 g/L $K_2HPO_4$, 0.5 g/L $MgSO_4 \cdot 7H_2O$, 0.1 g/L KCl and 0.1 g/L $Ca(NO_3)_2$, 30 g/L $FeSO_4 \cdot 7H_2O$), and were transferred to solid or liquid media supplemented with iron salts or sulfur after one week growing at 30 or 45° C., in order to characterize oxidizing microorganisms for one substrate or the other one.

Many mixed cultures were obtained and their specific activity for iron oxidation and soluble copper release was measured using atomic absorption spectrometry (AAS). The mixture with highest activity was selected from the previous cultures and was subjected to isolation of pure strains. When assaying each of the isolated strains, strain Wenelen DSM 16786 was found to show the best copper recovery from chalcopyrite when compared to other isolated strains and to bacteria from collections.

The strain named Wenelen DSM 16786 is a strictly acidophilic (pH <4.0), aerobic, mesophilic (26-35° C.) and gram-negative bacterium with bacillary morphology, having a size between 0.2 and 0.4 µm, chemolithotrophically growing in liquid 9K medium modified with ferrous ion, elemental sulfur or thiosulfate as the only energy sources, and showing a large oxidizing activity on ferrous ion and metallic sulfide species. The strain was taxonomically identified by 16S rDNA sequencing as an *Acidithiobacillus ferrooxidans* species (Kelly D P, Wood A P, "Reclassification of some species of thiobacillus to the newly designed genera *Acidithiobacillus* gen. nov., *Halothiobacillus* gen. nov and *Thermithiobacillus* gen. nov.", Int. J. Syst. Evol. Microbiol. 2000, 50, 511-516). Amplification of 16S rDNA gene was carried out by PCR using universal primers described in Coram, N., and Rawlings, D E, "Molecular relationship between two groups of the genus *Leptospirillum* and the finding that *Leptospirillum ferriphilum* sp. nov. dominates South African commercial biooxidation tanks that operate at 40.degree. C." Appl. Env. Microb., 2002, p. 838-845. The complete genome of strain Wenelen DSM 16786 was sequenced by a shot-gun library procedure and is being subjected to annotation at the moment. From this sequencing, a G+C content of 58.5% was determined. The strain was deposited and accepted Oct. 7, 2004 under the Budapest Treaty on the International Recognition of the Deposit of Microorganisms for the purpose of Patent Procedure in the Deutsche Sammlung von Mikroorganismen und Zellkulturen GmbH (DSMZ), having the address of Mascheroder Weg 1b, D-38124 Braunschweig, Germany. The strain was given the deposit (accession) number DSM 16786.

DESCRIPTION OF THE DRAWINGS

FIG. 1 shows the description of sequence SEQ ID No 1 belonging to the gene 16S rDNA amplified by PCR from extra-genomic DNA of Wenelen DSM 16786, which allowed the phylogenetic classification of the strain.

Lane Std.: λHind III molecular weight standard;
Lane 1: Wenelen DSM 16786 total DNA;
Lane "–": negative extraction control;
Lane 2: ATCC 23270 total DNA.

White arrows indicate the presence of plasmids in both strains.

This 1.5% agarose gel was loaded according to the following order:
Lane Std.: φX174/HaeIII molecular weight standard;
Lane "−": negative amplification control;
Lane 1: intergenic region amplicon from Wenelen DSM 16786 total DNA;
Lane 2: intergenic region amplicon from ATCC 23270 DNA.

A different banding pattern can be observed for each strain, which confirms the differences at genetic level.

Black circles represent the behavior of a blank or control consisting of non inoculated medium (abiotic), where copper extraction is minimal and due only to chemical leaching. Black triangles represent strain ATCC 23270, which is an *Acidithiobacillus ferrooxidans* strain like Wenelen strain. Black squares show the extraction percentage of copper due to the action of strain *A. ferrooxidans* Wenelen DSM 16786, its value being approximately 5% higher than collection strain ATCC 23270 after 41 days.

Figure 2:
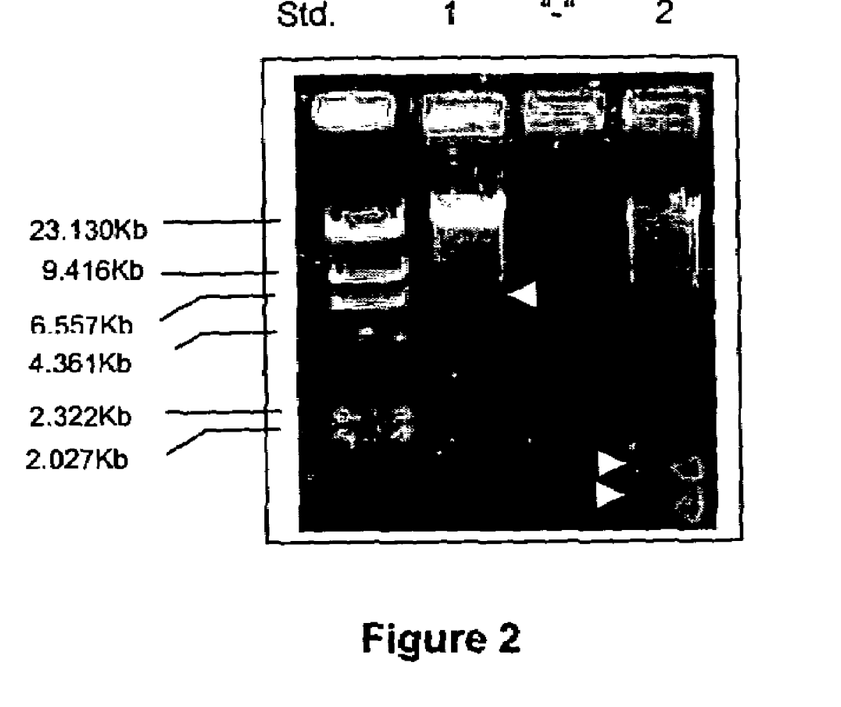
FIG. 2 shows a comparison between genomic material of strains *A. ferrooxidans* Wenelen DSM 16786 and ATCC 23270 using total DNA analysis extracted from both strains. This 1.5% agarose gel was loaded according to the following order.

FIG. 1 shows the sequence named SEQ ID No 1 that belongs to Wenelen DSM 16786 16S rDNA. There are many bacteria that have large homology differences in their complete genomes and therefore have large phenotypic differences even when they could be identical when their 16S rDNAs are compared. This is the case of strain Wenelen DSM 16786, which have a 100% homology in its 16S rDNA when compared to strain ATCC 23270, whose genome has been sequenced and deposited at the Institute of Genomic Research, US (NC_002923 2n GeneBank/RefSeq). However, as can be observed in FIG. 2, their genomic differences are obvious: in strain ATCC 23270 (lane 2) it is possible to distinguish two plasmids having a size lower than 2 Kb, whereas in Wenelen DSM 16786 (lane 1) only one plasmid having approximately 5 Kb is to be found. This information has been confirmed in the preliminary annotation of the bacteria being performed after sequencing, where a fragment of approximately 5 Kb has been detected with overlapping ends, which strongly suggests a plasmid-type circular structure. Sites that could be related to replication start and end, promoter and ribosome binding sites have also been detected in this sequence, which is a further argument that suggests the presence of a plasmid-type extra-chromosomal element.

Figure 3:
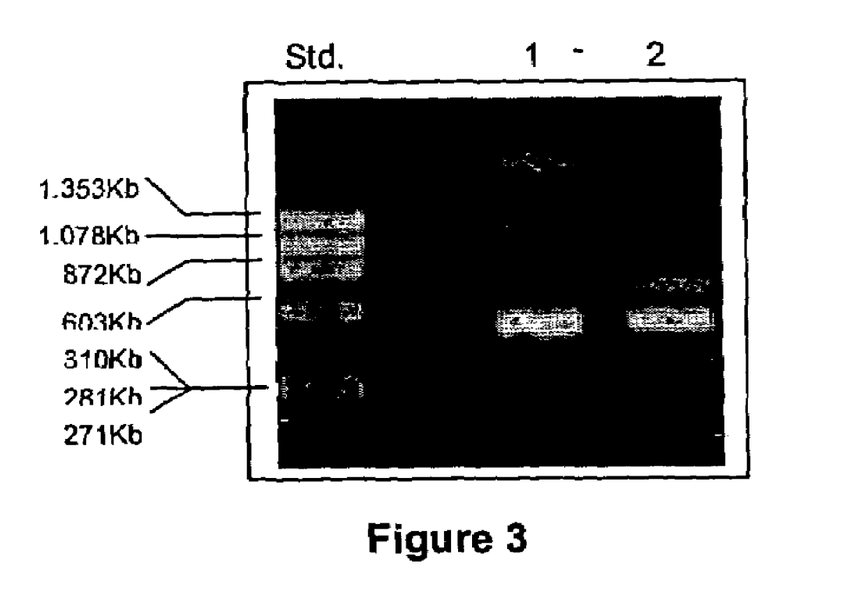
FIG. 3 shows a comparison between genomic material of strains *A. ferrooxidans* Wenelen DSM 16786 and ATCC 23270 using 16S-23S rRNA intergenic spacing region (ISR) amplification.

In FIG. 3 the difference between strains Wenelen DSM 16786 and ATCC 23270 is clearly evident, since in the amplification of intergenic region 16S-23S rRNA according to the protocol described by Pizarro et al. (in "Bacterial population in samples of bioleached copper ore as revealed by analysis of DNA obtained before and after cultivation", Applied and Environmental Microbiology, 1996, p1323-1328) a totally different banding pattern is observed for each strain.

After microbiological and taxonomical characterization, isolated strain Wenelen DSM 16786 was successfully used for leaching of minerals and sulfured metal concentrates, especially chalcopyrite, in stirred flasks, mini-columns, pilot columns and vats, tanks, heaps, dumps, tailing dams and in situ operations at industrial scale.

Likewise, mineral leaching tests were performed wherein mineral was inoculated with recycle solutions originating from solvent extraction plants containing strain Wenelen DSM 16786 of the present invention. This process was preferentially carried out at pH between 2 and 3 and temperatures between 20 and 50° C.

For inoculation purposes, strain Wenelen DSM 16786 could be cultured in tanks, reactors or heap of ores with addition of nutrients, air, oxygen-enriched air, carbon dioxide, carbonates and other elements favoring their growth.

Strain Wenelen DSM 16786 shows oxidizing activity in a temperature range between 10 and 60° C., more preferably between 25 and 50° C., and in a solution pH range between 1.3 and 4.0, more preferably between 1.6 and 2.8, so that process conditions have to be maintained in these ranges in order to obtain an optimum chalcopyrite oxidizing activity.

Strain Wenelen DSM 16786 can be inoculated on minerals where native strains are present and can be inoculated together with other strains, having an increased copper solubilization activity in both cases.

APPLICATION EXAMPLES

Example 1

The specific activity of isolated strain Wenelen DSM 16786 was measured in bioleaching of a copper mineral concentrate comprising chalcopyrite (84.69% by weight), which was obtained from a mine site at industrial level, according to the following experimental protocol:

1. Pre-cultured bacteria *Acidithiobacillus ferrooxidans* Wenelen DSM 16786 at a concentration of $10^7$ cells/ml were inoculated in a 500 ml flask with 150 ml of modified 9K medium at pH 2.5.

2. Up to 1% of a copper concentrate containing 84.69% (by weight) of chalcopyrite, with chemical composition indicated in Table 1 and mineralogical composition indicated in Table 2, was added to the inoculated medium. Only chemical compositions of the minerals are indicated in Table 1, since the remaining 35.45% correspond to gangue and trace elements.

3. The flask containing the aforementioned mix was incubated in an orbital shaker at 30° C. and 150 rpm during 41 days.

4. Copper contents in the leaching solution were measured by atomic absorption spectrometry in a Perkin Elmer AAnalist 400 equipment.

The same protocol was used to assay strain Wenelen DSM 16786, collection strain *Acidithiobacillus ferrooxidans* ATCC 23270 and a non inoculated sample for comparative purposes.

TABLE 1

Chemical Analysis of the Copper Concentrate

| | Element | | | | | | | |
|---|---|---|---|---|---|---|---|---|
| | Cu | Fe | S | Pb | Zn | SiO$_2$ | CaO | As |
| (% by weight) | 27.1 | 27.9 | 31.8 | 0.20 | 0.45 | 3.54 | 0.38 | 0.006 |

TABLE 2

Mineralogical Analysis of the Copper Concentrate

| Chalcopyrite | 84.69% |
|---|---|
| Pyrite | 3.91% |
| Chalcosite | 0.65% |
| Silicates | 10.75% |

Figure 4:
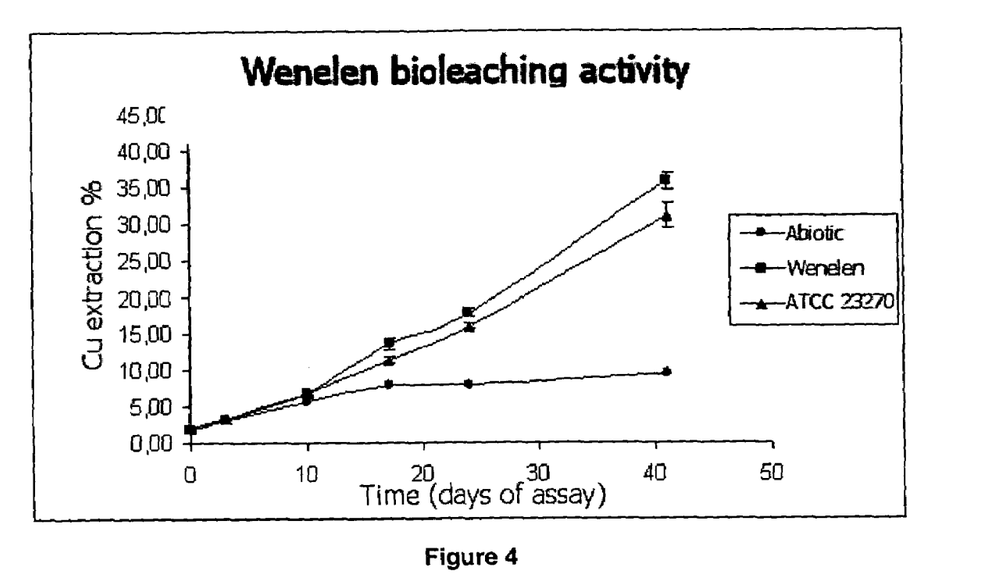
FIG. 4 shows the kinetics of bioleaching for a chalcopyrite concentrate.

In FIG. 4 results are shown for bioleaching of the copper concentrate by isolated strain Wenelen DSM 16786 and comparison with ATCC 23270, and a non inoculated control (blank). The bioleaching of strain Wenelen DSM 16786 has a higher slope than ATCC 23270, 0.8271 with correlation $R^2=0.9824$ in the first case and 0.7320 with $R^2=0.9825$ for the collection strain, reaching a copper recovery of approximately 35%, compared to less than 30%. The former facts are a clear indication of the higher chalcopyrite bioleaching activity showed by strain Wenelen DSM 16786 when compared to strain *Acidithiobacillus ferrooxidans* ATCC 23270, whose genome has been sequenced, and of course when compared to the non inoculated blank sample.

Example 2

Oxidizing activity on copper concentrate was measured in order to establish the influence of temperature and pH on the growth of isolated strain Wenelen DSM 16786, according to the following protocol:
1. Strain Wenelen DSM 16786 was cultured during 7 days in modified 9K medium.
2. Cells were filtrated through Toyo No. 5B filter paper in order to remove iron precipitates.
3. The filtrated cells were centrifuged at 15.000×g during 10 min and washed with a buffer solution of β-alanine-SO$_4^{2-}$ 0.1 M. An amount of cells corresponding to 0.1 g of total protein (Lowry et al., J Biol Chem. November 1951; 193 (1): 265-75) was resuspended in 1.0 ml of the same β-alanine-SO$_4^{2-}$ 0.1 M buffer.
4. A suspension of 50 mg of the copper concentrate described in Tables 1 and 2 was prepared in 1.0 ml of β-alanine-SO$_4^{2-}$ buffer at the required pH and temperature.
5. The reaction was started by adding the cells obtained in step 3 to the copper concentrate suspension, adjusting to a final volume of 2.5 ml.
6. The biological oxygen demand of the strain was measured under these conditions using a biological oxygen monitor that allows controlling the reaction temperature (Yellow Spring Instrument Co., Ohio, USA).

Figure 5:
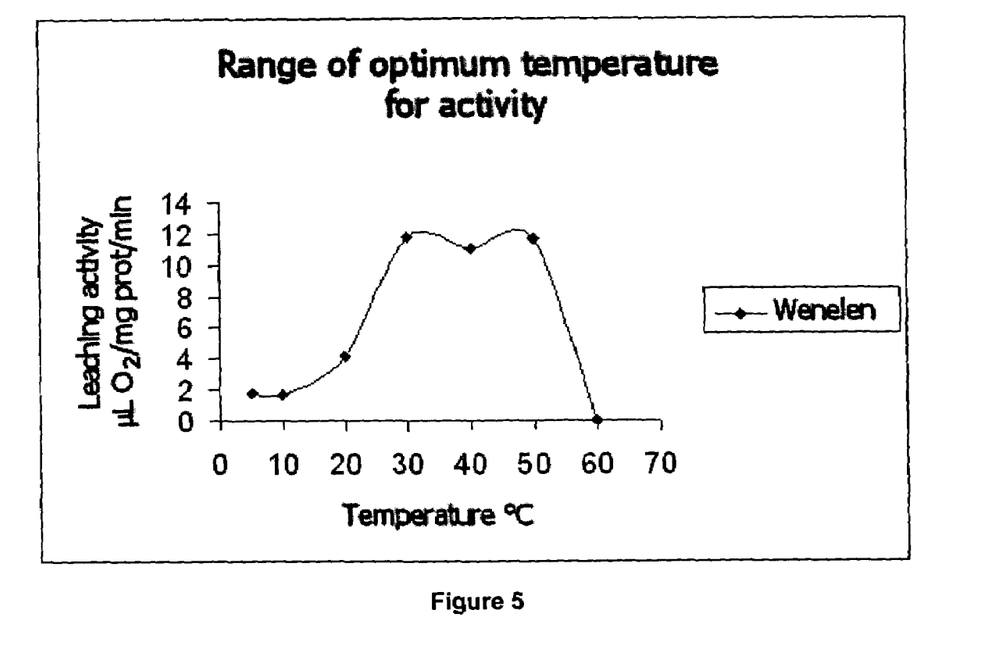
FIG. 5 shows the effect of temperature in the bioleaching activity of strain Wenelen DSM 16786. The curve represents the specific bioleaching activity in terms of $uIO_2$/mg protein/min for different temperatures (° C.). As can be observed, the optimum temperature range is between 26 and 55° C.
Figure 6:
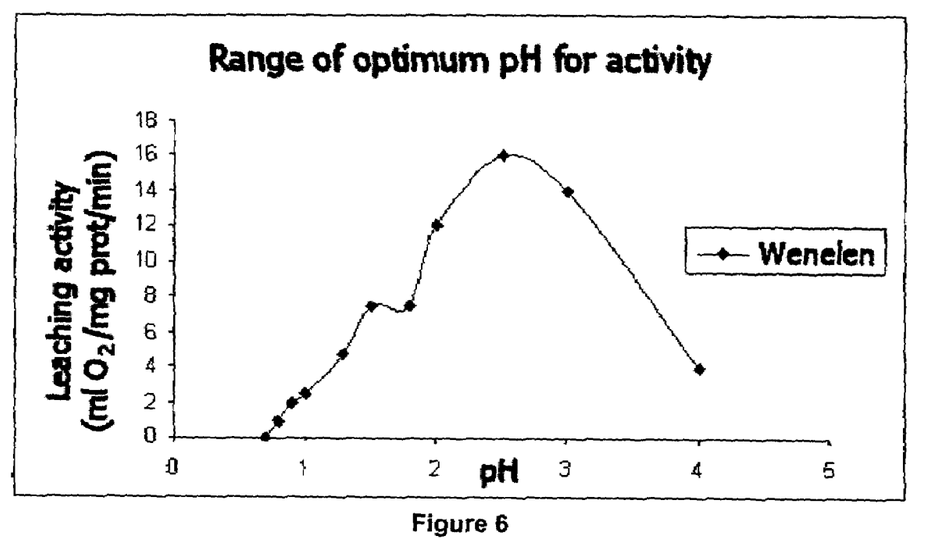
FIG. 6 shows the effect of pH in the bioleaching activity of isolated strain Wenelen DSM 16786. The curve shows the optimum pH range for which bioleaching activity is higher. This range is comprised between 1.5 and 3.5.

The results for the assay are shown in FIGS. 5 and 6. These figures show that the optimum oxidation conditions for strain Wenelen DSM 16786 are in the temperature range between 10 and 60° C., and in the pH range between 1.3 and 4.0.

FIG. 5 shows the effect of temperature over copper sulfide oxidizing activity at pH 3.0. Evidently, strain Wenelen DSM 16786 shows a higher activity between 20 and 50° C.

FIG. 6 shows the effect of pH over copper sulfide oxidizing activity at 30° C. Evidently, strain Wenelen DSM 16786 shows an optimum activity in a pH range between 2 and 3.

Example 3

An experiment was carried out in order to compare bioleaching activity of isolated strain Wenelen DSM 16786 on a copper sulfide ore sample in a bioleaching mini-column having a non flooded ore bed simulating industrial conditions for mineral processing in heap or dump leaching, when compared to other collection strain of the same species (strain ATCC 23270), according to the following protocol:
1. Columns were made using polyvinyl chloride tubes having 40 mm diameter and 20 cm height.
2. The columns were packed with 225 g of mineral comprising mainly chalcopyrite and bornite and having the characteristics described in Table 3.
3. The inoculated cells were previously washed with irrigation buffer (3.0 g/L (NH$_4$)$_2$SO$_4$, 0.5 g/L K$_2$HPO$_4$, 0.5 g/L MgSO$_4$·7H$_2$O, 0.1 g/L KCl and 0.1 g/l Ca(NO$_3$)$_2$, 6 g/L FeSO$_4$·7H$_2$O, pH 2.5) and resuspended in 0.5 ml buffer. The amount of inoculated cells was 2×10$^9$ total cells for each column.
4. One of the columns was not inoculated and was maintained as a control.
5. Irrigation rate was established at 0.20 ml/min for each column.
6. The columns were kept at room temperature (22° C).
7. Samples were taken at 24 hours intervals during 7 days, and copper was measured in the leaching solution using atomic absorption spectrophotometry.

TABLE 3

Mineralogical Composition (100% Opaque Mineral and Gangue)

| | % | | | | | | |
|---|---|---|---|---|---|---|---|
| Minerals | Weight | % Vol. | % Cu | % Fe | % S | % Mo | % As |
| Chalcopyrite | 1.40 | 0.92 | 0.49 | 0.43 | 0.49 | | |
| Chalcosite | 0.03 | 0.01 | 0.02 | | 0.01 | | |
| Bornite | 1:16 | 0.63 | 0.74 | 0.13 | 0.30 | | |
| Gray copper | 0.02 | 0.01 | 0.01 | | 0.00 | | 0.00 |
| Pyrite | 0.50 | 0.27 | | 0.23 | 0.26 | | |
| Molibdenite | 0.06 | 0.03 | | | 0.02 | 0.03 | |
| Magnetite | 0.23 | 0.12 | | 0.17 | | | |
| Rutile | 0.10 | 0.06 | | | | | |
| Gangue | 96.50 | 97.94 | | | | | |
| Total | 100.00 | 100.00 | 1.26 | 0.95 | 1.09 | 0.03 | 0.00 |

Figure 7:
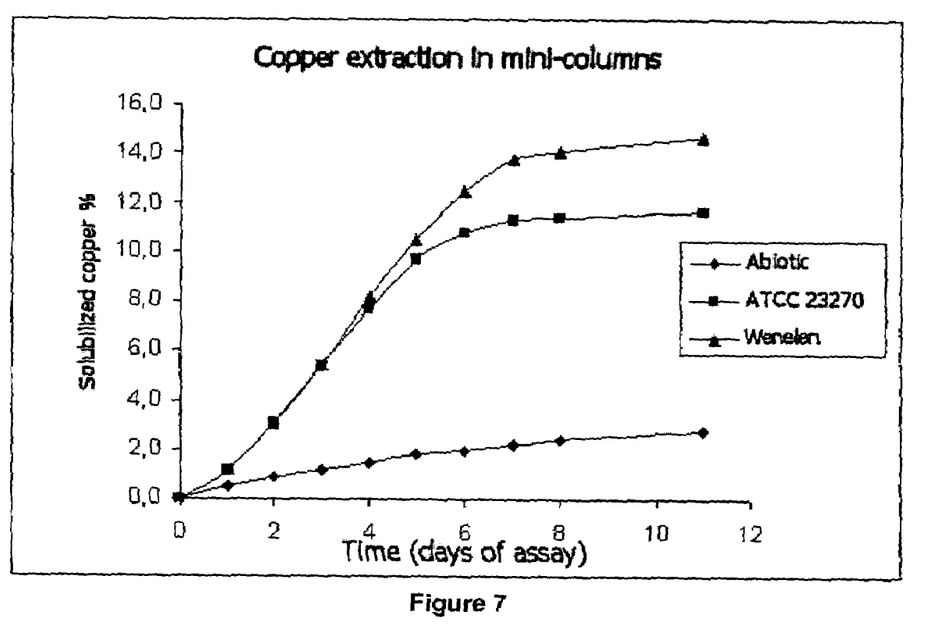
FIG. 7 shows the bioleaching activity of strain Wenelen DSM 16786 and collection strain ATCC 23270 belonging to the same species in a mini column assay with ores in a non flooded bed.

As shown in FIG. 7, bacteria have a clear effect on the amount of copper leached from the mineral when the curve without inoculum (approximately 3%) is compared with the curves of copper solubilized in the presence of bacteria (between approximately 12 and 15% after 11 days), strain Wenelen DSM 16786 presenting the highest bioleaching activity expressed as the increase of copper recovery observed when compared to collection strains.

Taking into account the copper containing mineralogical species present in the mineral, in Table 3, said species are bornite (59%) and chalcopyrite (39%). The bioleaching rate of bornite can be represented, in the presence of microorganisms, by reaction (1) (Peters, E., 1976, "Direct Leaching of Sulfides: Chemistry and Applications"):

Bornite: $Cu_5FeS_4 + 2Fe_2(SO_4)_3 \rightarrow Cu_3FeS_4 + 2CuSO_4 + 4FeSO_4$  (1)

The rate of oxidation of bornite is fast in the presence of ferric ions (chemical leaching) for the release of the first two copper atoms, whereas the intermediate compound of bornite leaching is readily transformed into chalcopyrite and covellite according to reaction (2):

$$Cu_3FeS_4 + 2Fe_2(SO_4)_3 \rightarrow CuFeS_2 + 2CuS + 4FeSO_4 \quad (2)$$

Both resulting covellite and chalcopyrite are slowly leached in the presence of ferric ions and bacteria, following reactions (3) and (4):

(3)

(4)

Based on the previous reactions, it is obvious that the first stages of the mineral bioleaching process, FIG. 7, are associated to reactions (1) and (2), which correspond to chemical leaching of bornite, wherein no substantial differences are observed between the used strains. The difference between strains is remarkable as long as the process is associated to leaching of resulting covellite and chalcopyrite, wherein the presence and activity of bacteria is fundamental, as shown in the Example 1 hereinabove described.

On the other hand, it is well known that bioleaching rate decreases as extraction increases, because as mineralogical species located at the surface of the mineral particles are leached, the rate of the process is controlled by the diffusion (the slowest stage) of the leaching agents and microorganisms into the mineral pores in order to access the metal located inside the particles, instead of the rate of microorganism-assisted oxidation control (named chemical control) in the first stages of the process.

Based on the previous analysis and in order to compare the bioleaching activities of *A. ferrooxidans* strains ATCC 23270 and Wenelen DSM 16876 represented in FIG. 7, it is necessary to determine the value of the kinetic constants for each microorganism (each case in FIG. 7), based on a liquid-solid reaction model with a non-reacting core controlled by chemical reaction, by correlating the extracted copper fraction $X_b$ for each time according to equation (5) (Levenspiel, O., "Chemical Reaction Engineering", Wiley, 1962 (First Edition), pp 344-350):

$$1/\tau = 1 - (1 - X_b)^{1/3} \quad (5)$$

wherein (1/tau) represents the time required to extract all the copper contained in the mineral particle. The results for copper extraction were correlated using equation (5), which gave the values for (1/tau) shown in Table 4, with correlation coefficients $R^2 = 0.9918$, 0.895 and 0.986 for strains Wenelen DSM 16876 and ATCC 23270 and the abiotic control, respectively.

TABLE 4

Specific Bioleaching Rate and Bioleaching Times for the Mixed Mineral Used in Example 2.

| | | Time to reach extraction | | |
|---|---|---|---|---|
| | | 30% | 50% | 100% |
| Bioleaching strain | 1/tau | | [days] | |
| Abiotic control | 1111 | 125 | 229 | 1111 |
| ATCC 23270 | 238 | 27 | 49 | 238 |
| Wenelen DSM 16786 | 182 | 20 | 38 | 182 |

The results shown in Table 4 indicate that strain DSM 16786 has a specific mineral bioleaching rate approximately 30% higher than strain ATCC 23270, which is reflected by the times required to extract all the copper contained in the mineral, namely 182 days compared to 238 days. For example, to recover 50% of copper 38 days would be required instead of 49 days required by the collection strain.

It is well known in mining industry that the main problem for the operation of leaching piles or heaps of sulfured minerals is the relatively slow metal recovery rate. A 30% increase in copper extraction rates, as in this example, would lead to savings of approximately 20-40% in bioleaching process costs at industrial scale (which at the moment are between 10 and 15 US¢/lb of fine copper), because the higher rates require a smaller mineral inventory, have smaller bombing, aeration and irrigation costs, have a higher copper concentration in the solutions conveyed to Solvent Extraction Plants, etc. In the case of bacterial leaching operations of sulfured minerals at Quebrada Blanca, $1^{st}$ Region, Chile, which produces approximately 200 tons of fine copper per day, these savings could represent 40-90 million dollars during the remaining operational life of this mining project.

What is claimed is:

1. An isolated bacterial strain wherein said bacterial strain belongs to the species *Acidithiobacillus ferrooxidans*, named Wenelen deposited as DSM 16786 at the DSMZ (Deutsche Sammlung von Mikroorganismen und Zellkulturen GmbH, Braunschweig, Germany), said DSM 16786 strain being a bacillary gram-negative bacterium that grows chemolithotrophically by oxidizing iron, elemental sulfur and compounds resulting from bioleaching of sulfide minerals or ores, and said strain has the 16S rDNA sequence of SEQ ID NO.1 and an extra-chromosomal element of approximately 15 Kb with an autonomous replication sequence; and said Wenelen DSM 16786 strain having an increased activity for leaching of metallic sulfide ores.

2. The isolated bacterial strain according to claim 1 wherein said bacterial strain has an increased activity for copper leaching from mixed sulfide ores.

3. The isolated bacterial strain of claim 2 wherein the mixed sulfide ore comprises chalcopyrite, bornite or covellite.

4. The isolated bacterial strain of claim 2 wherein the mixed sulfide ore comprises copper containing mineralogical species.

5. The isolated bacterial strain of claim 1 wherein the culture is effective to leach copper from metallic sulfide ores.

6. The isolated bacterial strain of claim 1 wherein the strain is the biologically pure culture of *Acidithiobacillus ferrooxidans* Wenelen DSM 16786.

* * * * *

SEQUENCE LISTING

<160> NUMBER OF SEQ ID NOS: 1

<210> SEQ ID NO 1
<211> LENGTH: 1531
<212> TYPE: DNA
<213> ORGANISM: Bacteria

<400> SEQUENCE: 1

```
tggagagttt gatcctggct cagattgaac gctggcggca tgcctaacac atgcaagtcg      60
aacggtaaca ggtcttcgga tgctgacgag tggcggacgg gtgagtaatg cgtaggaatc     120
tgtcttttag tggggacaa cccagggaaa cttgggctaa taccgcatga gccctgaggg     180
ggaaagcggg ggatcttcgg acctcgcgct aagagaggag cctacgtccg attagctagt     240
```

-continued

```
tggcggggta aaggcccacc aaggcgacga tcggtagctg gtctgagagg acgaccagcc      300
acactgggac tgagacacgg cccagactcc tacgggaggc agcagtgggg aattttcgc       360 aatgggggca accctgacga agcaatgccg cgtggatgaa gaaggccttc gggttgtaaa      420
gtcctttcgt ggaggacgaa aaggtgggtt ctaatacaat ctgctattga cgtgaatcca     480
agaagaagca ccggctaact ccgtgccagc agccgcggta atacgggggg tgcaagcgtt      540
aatcggaatc actgggcgta aagggtgcgt aggcggtacg ttaggtctgt cgtgaaatcc     600
ccgggctcaa cctgggaatg gcggtggaaa ccggtgtact agagtatggg agagggtggt    660
ggaattccag gtgtagcggt gaaatgcgta gagatctgga ggaacatcag tggcgaaggc    720
ggccacctgg cccaatactg acgctgaggc acgaaagcgt ggggagcaaa caggattaga    780
taccctggta gtccacgccc taaacgatga atactagatg tttggtgcct agcgtactga    840
gtgtcgtagc taacgcgata agtattccgc ctgggaagta cggccgcaag gttaaaactc    900
aaaggaattg acgggggccc gcacaagcgg tggagcatgt ggtttaattc gatgcaacgc   960
gaagaacctt acctgggctt gacatgtccg gaattctgca gagatgcgga agtgcccttc   1020
ggggaatcgg aacacaggtg ctgcatggct gtcgtcagct cgtgtcgtga gatgttgggt    1080
taagtcccgc aacgagcgca accttgtcc ttagttgcca gcggttcggc cgggcactct   1140
agggagactg ccggtgacaa accggaggaa ggtggggatg acgtcaagtc ctcatggcct   1200
ttatgtccag ggctacacac gtgctacaat ggcgcgtaca gagggaagcc aagccgcgag    1260
gtggagcaga ccccagaaag cgcgtcgtag ttcggattgc agtctgcaac tcgactgcat    1320
gaagtcggaa tcgctagtaa tcgcggatca gcatgccgcg gtgaatacgt tcccgggcct    1380
tgtacacacc gcccgtcaca ccatgggagt ggattgtacc agaagcagct agcctaacct    1440
tcgggagggc ggttaccacg gtatggttca tgactggggt gaagtcgtaa caaggtagcc    1500 gtagggaac  ctgcggctgg atcacctcct t                                    1531
```